United States Patent [19]
Clement

[11] Patent Number: 5,217,468
[45] Date of Patent: Jun. 8, 1993

[54] TISSUE ENCAPSULATING SHEATH

[75] Inventor: Thomas P. Clement, Bloomington, Ind.

[73] Assignee: Mectra Labs, Inc., Bloomfield, Ind.

[21] Appl. No.: 782,379

[22] Filed: Oct. 24, 1991

[51] Int. Cl.$^5$ ............................................. A61B 17/22
[52] U.S. Cl. ..................................... 606/127; 606/206; 606/114
[58] Field of Search ............... 606/127, 128, 114, 106, 606/206

[56] References Cited

U.S. PATENT DOCUMENTS

| | | | |
|---|---|---|---|
| 2,623,152 | 12/1952 | Ammon | 606/206 X |
| 3,074,408 | 1/1963 | Chester | 606/127 |
| 3,827,437 | 8/1974 | Inaba | 606/127 X |
| 3,870,048 | 3/1975 | Yoon | 606/206 X |
| 4,243,040 | 1/1981 | Beecher . | |
| 4,509,517 | 4/1985 | Zibelin | 606/127 |
| 4,611,594 | 9/1986 | Grayhack et al. | 606/127 |
| 4,865,030 | 9/1989 | Polyak | 606/127 X |
| 4,927,426 | 5/1990 | Dretler . | |
| 4,997,435 | 3/1991 | Demeter | 606/127 |

FOREIGN PATENT DOCUMENTS

| | | | |
|---|---|---|---|
| 1566147 | 7/1970 | Fed. Rep. of Germany | 606/127 |
| 3006027 | 11/1981 | Fed. Rep. of Germany | 606/127 |
| 725001 | 3/1955 | United Kingdom | 606/106 |

Primary Examiner—Peter A. Aschenbrenner
Attorney, Agent, or Firm—Barnes & Thornburg

[57] ABSTRACT

A tissue retrieval apparatus for laparoscopic procedures includes a longitudinally extending tube having a tip end insertible into a patient. The tip end is formed to be radially expandable in response to withdrawal of tissue into the tip end of the tube. Tissue can be withdrawn into the tip end of the tube by using graspers or other devices that can be extended to engage and hold tissue. To reduce the possibility of contamination of healthy tissue, an elastic sheath is attached to cover the tip end of the tube. The elastic sheath is formed to radially expand in response to radial expansion of the tip end of the tube during withdrawal of tissue into the tip end of the tube.

25 Claims, 3 Drawing Sheets

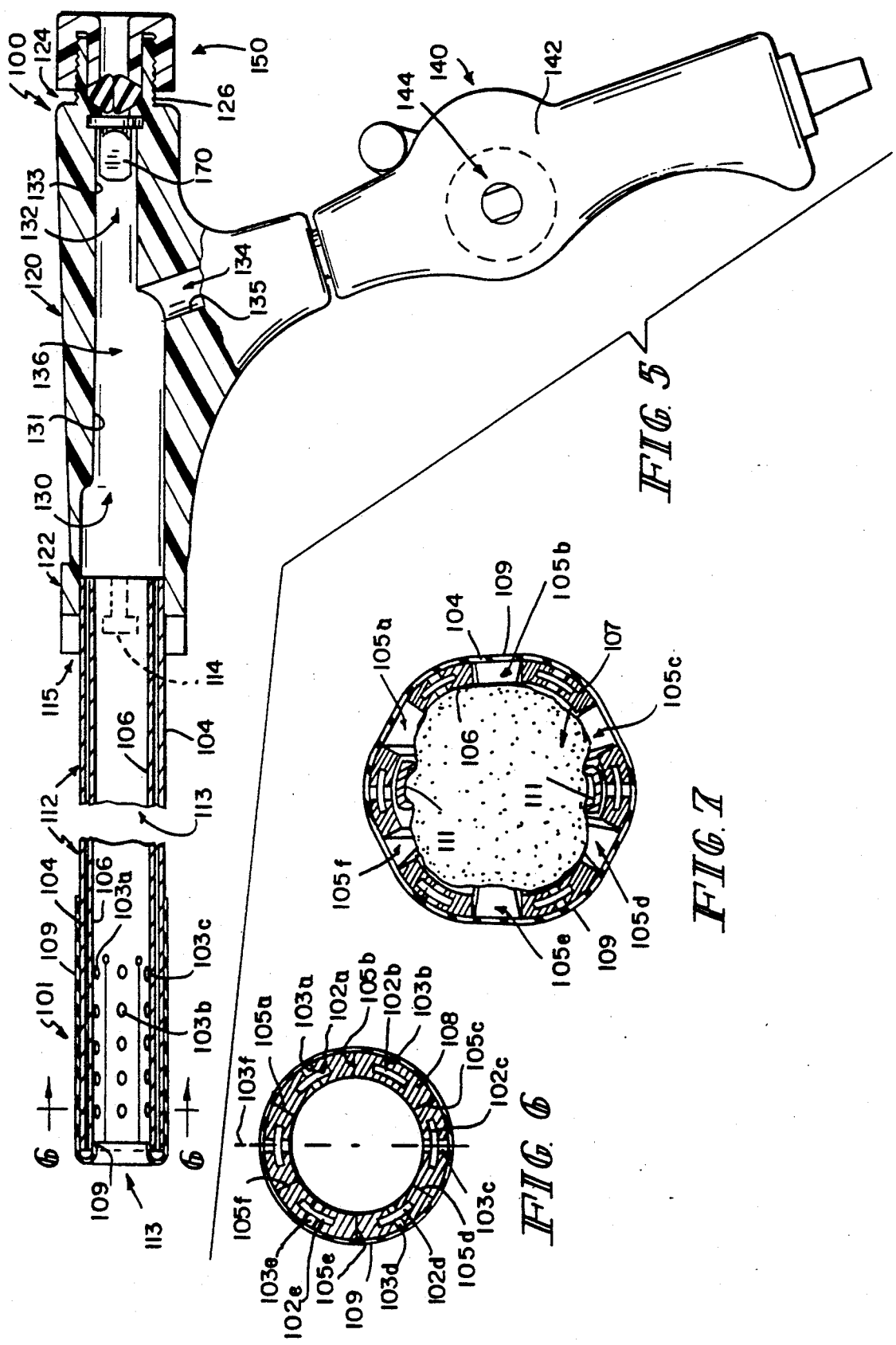

TISSUE ENCAPSULATING SHEATH

BACKGROUND AND SUMMARY OF THE INVENTION

This invention relates to an apparatus for removing tissue or organs from a patient's body. More particularly, this invention relates to laparoscopic instrument having an encapsulating sheath to aid in capture and withdrawal of tissue or organs.

Laparoscopic surgery often requires dissection or severance of diseased or otherwise infected organs or tissue present in a patient's abdominal cavity. However, retrieval of the dissected or severed tissue or organs can present problems of contamination of overlying abdominal muscle tissue when the tissue is removed from the patient's body. When the laparoscopic instrument is withdrawn from a patient's body, bits of diseased tissue can contact and possibly infect the remaining healthy tissue as the laparoscopic instrument is withdrawn from the surgical site. While many laparoscopic devices are known for grasping and retracting severed organs or tissues, none provides a simple mechanism for sterile screening or shielding of healthy tissue from severed, diseased tissue during retraction of the laparoscopic instrument from the patient's abdomen.

In the field of urology, devices are known for encapsulating and extracting kidney stones from human body passages. Generally, only small pieces of stone are retracted using these devices because of the small size (device size is limited by the small radius of the relevant body passageways) of the urological devices. A typical urological device has a catheter that is generally no greater than 4 mm to allow its ready entrance and movement along the body passageways.

For example, U.S. Pat. No. 4,927,426, issued to Dretler on May 22, 1990, describes a catheter device for capturing and holding kidney stones. This catheter is formed from an elongated tube having a cuff portion disposed on one end. The cuff portion can be actuatably collapsed inward into the tube and a snare is disposed and actuatably movable within the catheter for capturing and holding a kidney stone and collapsing the cuff portion to surround the kidney stone. However, rather than risking injury to narrow body passages by withdrawing an ensnared kidney stone, the kidney stone is typically disintegrated in place in the body passage using known lithotriptic methods.

U.S. Pat. No. 4,611,594 issued Sep. 16, 1986 to Grayhack et al. also discloses an instrument useful for containment of calculi found in body passages or organs. In one embodiment of the disclosed apparatus, the distal end portion of a catheter is provided with several expandable gussets that permit enlargement of the catheter's distal end as the working end of the grasping device, and any stone grasped therein, are retracted into the catheter. In other embodiments disclosed, struts of an open-ended basket are bridged by a flexible membrane or web that can close over calculi.

U.S. Pat. No. 4,997,435, issued Mar. 5, 1991 to Demeter, discloses a percutaneous catheter with an encapsulating receptacle. Several struts extend from their attachment to a first catheter, giving a cup-shaped form. A sheath is attached to cover the struts.

U.S. Pat. No. 4,243,040, issued Jan. 6, 1981 to Beecher, discloses a device for removing objects from human body passages. The disclosed device is useful for removing kidney stones, gall stones, and other objects from human body passages. A thin, rubber, tubular sleeve inflatable by fluid pressure, forms a soft annular convex portion that bulges beyond a distal end of a inner tube for receiving engagement with a stone. The stone is captured by suction applied by the inner tube. The inner tube is retracted into the sleeve while progressively turning the sleeve inside out around the stone to envelop it for removal from the tubes.

In contrast to these small diameter urological devices, the present invention is a tissue or organ retrieval apparatus particularly useful for retrieving large bits of tissue or even small organs (for example gall bladders and ovaries) during laparoscopic procedures. The apparatus includes a longitudinally extending tube having a tip end insertible into a patient. The tip end of the tube is quite large compared to urological devices, often having a diameter of between about 5 mm to about 15 mm or more, although it is more typically from about 5 mm to about 9 mm in diameter. The tip end of the longitudinally extending tube is formed to be radially expandable in response to withdrawal of tissue into the tip end of the tube.

Tissue can be withdrawn into the tip end of the tube by using graspers, pincers, nets, baskets, suction applying devices or any other device that can be extended to engage and hold tissues or organs with sufficient force. To reduce the possibility of contamination of healthy tissue, an elastic sheath is attached (typically by welding or with an elastic adhesive) to cover the tip end of the tube. The elastic sheath is formed to radially expand in response to radial expansion of the tip end of the tube during withdrawal of tissue into the tip end of the tube.

In preferred embodiments of the invention, four peripherally spaced, longitudinally directed slits are symmetrically arranged about the tip end of the tube to promote substantially even radial expansion of the tip end of the tube. A reciprocally movable grasper may be positioned to extend through the longitudinally extending tube. The grasper may be formed to define a pair of movable, opposing jaws that can be mechanically urged together for grabbing and holding severed or dissected tissue as the tissue is drawn into the tip end of the tube. As indicated above, a number of different types of devices may be used to grasp or hold a piece of tissue or an organ to pull it up into the tip end of the tube.

Another embodiment of the present invention provides a laparoscopy device for use in surgical operations in which an organ is severed from the body. The device includes a tubular element for penetrating into the body. The tubular element has a proximal end portion outside the body and a distal end portion inside the body adjacent the organ to be removed, and further defines a central axial passageway through which various surgical instruments are inserted from outside the body to the organ to be removed. The distal end portion of the tube is formed to resiliently expand radially outwardly. For instance, the tube may be formed to have a grasper for grasping the severed organ and pulling it into the distal end portion of the tubular element to be held by said finger portions is provided, and a flexible, elastic sheath covering the distal end portion is also provided. The sheath has an open end mating with the open end of the distal end portion so that when the severed organ is grasped and pulled into the distal end portion the sheath encloses the distal end portion, grasper and severed organ for removal from the body.

Still another embodiment of the present invention provides a tissue retrieval apparatus for removal of tissue from a patient's body. The apparatus includes a cannula formed to define a channel therethrough, the cannula having an outer wall and an inner wall, and a plurality of ribs longitudinally extending to connect the outer wall and the inner wall. Channels are also defined between adjoining ribs. The cannula has a tip end insertible into a patient, with the tip end of the cannula being formed to define a plurality of longitudinally directed slits to allow expansion of the tip end of the cannula in response to withdrawal of tissue into the tip end of the cannula. A mechanism is provided for withdrawing tissue into the tip end of the cannula. Preferably, graspers, tweezers, suction, or other conventional mechanisms are used. In addition, an elastic sheath is attached to cover the tip end of the cannula. The elastic sheath is formed to expand in response to expansion of the tip end of the cannula upon withdrawal of tissue into the tip end.

In preferred embodiments, the withdrawing mechanism includes a conduit piece formed to define at least one passageway. This conduit piece is connected in fluid communication with the channels of the cannula to allow passage therethrough of grasping instruments, and/or suction intake of tissues or fluids. The conduit piece may be sealed, and may also have a valve mechanism for controlling fluid flow in the at least one passageway of the conduit piece. In certain embodiments, the conduit piece is formed to define first, second, and third passageways, the first passageway being connected to the channels of the cannula, the second passageway being connected to the sealing mechanism, and the third passageway being connected to the valve mechanism.

The sealing mechanism may include a compressible annular seal positioned to seal the second passageway, a mechanism for compressing the compressible annular seal to provide an airtight seal across the second passageway, and a duckbill flap valve positioned in the second passageway. The duckbill flap valve may have first and a second flaps biased to sealingly engage each other, the first and second flaps being configured to move apart to permit passage therethrough of a medical device (such as graspers, secondary cannulas, etc.) inserted through the conduit piece.

The foregoing described embodiments and other aspects of the invention will be better understood with reference to the following description of the drawings.

BRIEF DESCRIPTION OF THE DRAWINGS

FIG. 5 is a side view of a cannula assembly, partially cut away to illustrate passageways defined in an interior of a conduit piece, the passageways of the conduit piece connecting to a cannula, to a valve mechanism, and to a sealing assembly that includes a compressible annular seal and a duckbill flap valve;

FIG. 6 is a traverse cross sectional view along line 6—6 of the tip end of the cannula shown in FIG. 5, illustrating an elastic sheath surrounding the cannula, a large interior channel defined in the cannula to connect with the conduit piece, and a plurality of channels defined between ribs of the cannula, the ribs separating and supporting the inner and outer walls of the cannula;

FIG. 7 is a view of the tip end of the cannula shown in FIG. 5, shown with tissue being drawn into the interior channel of the cannula, and the cannula radially expanding by separation at slits symmetrically defined about the tip end;

DETAILED DESCRIPTION OF THE INVENTION

Figure 1:
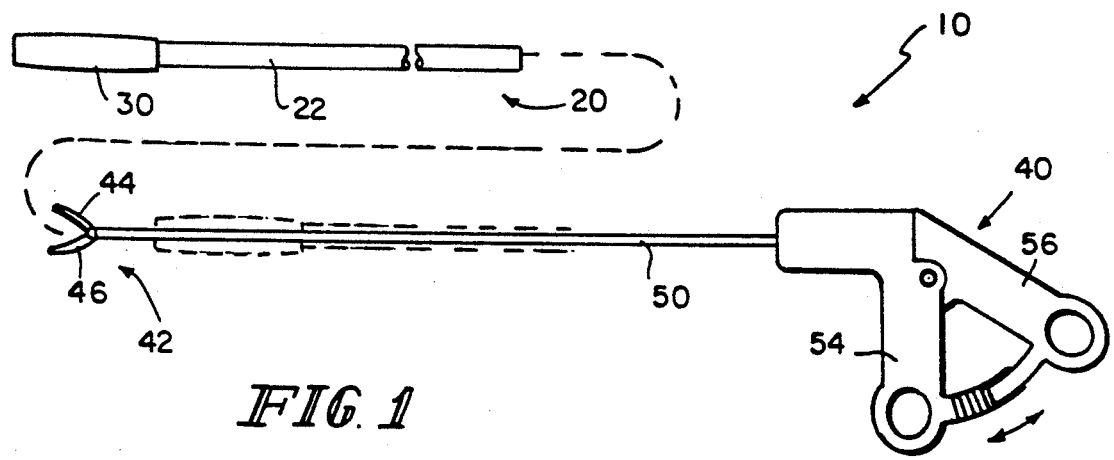
FIG. 1 is a view of a tissue retrieval apparatus and a disposable tissue cover for placement over a cannula of a grasping apparatus.

FIG. 1 illustrates a tissue retrieval apparatus 10. The apparatus 10 includes a tissue cover 20 that is removably fittable over a cannula 50 of a grasping apparatus 40. Both the tissue cover 20 and the grasping apparatus 40 are constructed of low-cost, disposable materials. The tissue retrieval apparatus 10 is typically sterilized, conveyed to an end-user, and discarded as medical waste after one surgical use by a surgeon or medical technician. Use of disposable apparatus 10 reduces the chance of infection associated with re-use of non-disposable instruments and is preferred for the present invention.

The illustrative grasping apparatus 40, typical of those known to those skilled in the art, includes a grasper 42 attached to a cannula 50. The grasper 42 is provided with first and second jaws 44 and 46, respectively having serrations 48 to aid in gripping soft tissues and organs. The cannula 50 is attached to a handle 54 designed to be grasped by a surgeon or other operator. A lever arm 56 is pivotably attached to both the handle 54 and to rod 52. Squeezing lever arm 56 toward handle 54, or moving lever arm 56 away from handle 54, alternately acts to push or pull the rod 52 toward or away from the handle 54. Movement of the rod 52, in turn, opens and closes opposing first and second jaws 44 and 46 of grasper 42.

The tissue cover 20 is designed for single use applications. The tissue cover 20 includes a longitudinally extending tube 22 that is formed to define a cavity 23 therethrough. Preferably, the tube 22 is formed from a single extruded piece of a biocompatible plastic material, such as polypropylene, polyethylene, or other thermoset plastics. However, composite, layered, or metallic materials can be used to form tube 22. Constructing the tube 22 from extruded biocompatible plastic is advantageous because of the cost savings, and ease of forming plastic materials.

Figure 2:
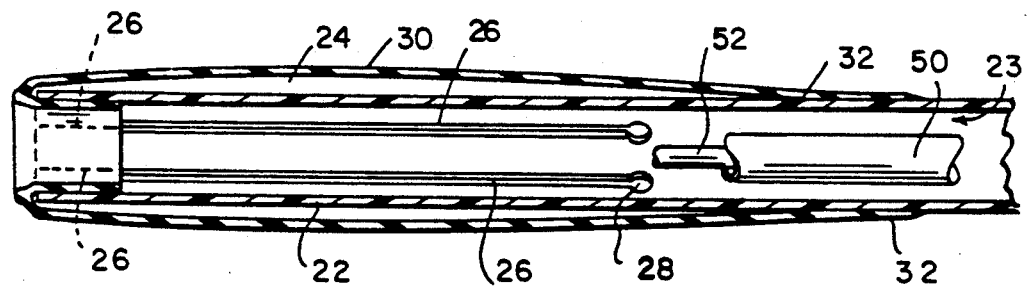
FIG. 2 is a view of the tip end of the tissue retrieval apparatus with the disposable tissue cover positioned over the cannula of the grasping apparatus.
Figure 3:
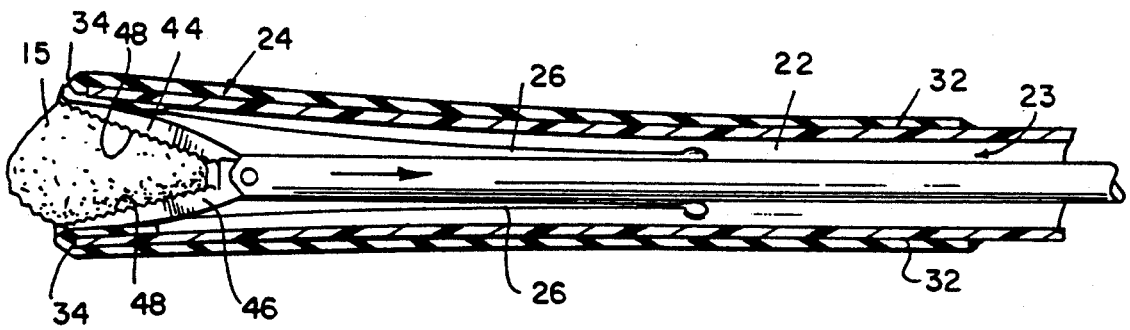
FIG. 3 is an enlarged view of the tip end of the tissue retrieval apparatus, showing a grasper engaging and drawing a piece of tissue into the tip end of the tissue cover.
Figure 4:
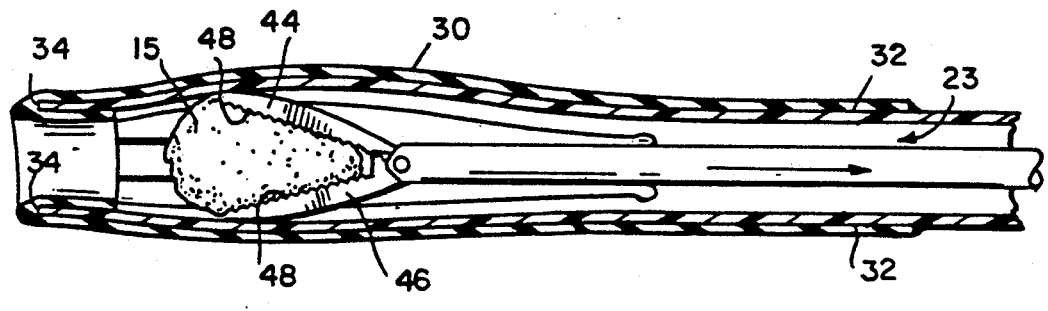
FIG. 4 is an enlarged view of the tip end of the tissue retrieval apparatus, shown with the tissue fully withdrawn into the tip end, and with an elastic sheath of the disposable tissue cover surrounding the tissue.

As shown in FIGS. 2–4, four peripherally spaced apart, symmetrically arranged longitudinal slits 26 are defined in the tip end 24 of the tube 22. Typically, when the tube 22 is constructed of plastic, these slits 26 are not formed during molding or extrusion process. Instead, after tube 22 is formed, multiple cuts are made along the longitudinal axis of the longitudinally extending tube 22, to define the slits 26. Each slit is about the same length in the illustrated embodiment, although it is of course possible to cut slits having varying lengths relative to each other. For laparoscopic applications, the length of slits 26 are generally equivalent to each other, and are selected to range from about 20 mm to about 100 mm, although lengths of about 20 mm to about 60 mm are more generally required. Longer slit lengths allow accommodation and retrieval of larger volumes of tissue, but can result in low rigidity of tube 22. The longitudinal slits 26 each terminate in apertures 28 defined in the tip end 24 of the tube 22. The apertures 28 are circular, and act to reduce problems with stress crack propagation along the tube 22 because of the longitudinal slits 26 cut into that tube.

Completely covering the longitudinal slits 26 is an elastic sheath 30. Like the tube 22, the elastic sheath 30 is generally formed from a biocompatible plastic. Unlike the tube 22, which must be somewhat rigid to allow probing action and retraction from the abdomen, the sheath 30 is formed from a sheet of very thin and flexible polymeric material such as latex. The elastic sheath 30 can be formed from a ingle sheet of latex or other flexible material wrapped around to weldingly join a pair of its opposed edges, or can be formed as one piece by extrusion. To ensure greatest structural strength, in preferred embodiments the sheath 30 is formed from a single piece of elastic material.

The elastic sheath 30 is weldingly attached to tube 22 along weld 32 indicated in the Figures. Welding can be by radio frequency methods, ultrasonic, heat, or any other method for providing a smooth, tight seal between the sheath 30 and the tube 22. The elastic sheath 30 is also attached at its other end by an adhesive 34 to the tube 22. As shown in the Figures, the sheath 30 is folded around tube 22 and attached to the inside of the tube 22. Preferably, an elastic adhesive is used to allow stretching attachment of the sheath 30 to the tube 22.

For use in laparoscopic procedures, the tip end 24 of the tube 22, covered by the elastic sheath 30, is inserted into the abdominal cavity through a perforation made by a trocar or other conventional piercing instrument. This is best seen in FIG. 2, which illustrates (moving from outside to the center) the elastic sheath 30 surrounding a tube 22, and tube 22 surrounding a cannula 50 that supports graspers (shown in FIG. 3 and 4) operated by movement of rod 52 disposed in the cannula 50. After a piece of tissue has been cut away from a patient's body, the cannula 50 is moved to extend outward from the tip end 24 of the tube 22. The grasper 42 is worked to grasp a piece of tissue 15 between its opposing jaws 44 and 46, and, while holding the tissue cover 20 motionless relative to the patient, the cannula 50 is withdrawn into the tip end 24 of the tube 22.

As shown in FIG. 3, pulling the grasper 42, and the tissue 15 held by the grasper 42, back into the tip end 24 of the tube 22 causes outward movement of the tip end 24 of the tube 22. Because the slits 26 are radially symmetrically cut in the tube 22, the tip end 24 of the tube 22 smoothly and radially expands outward. As the tip end 24 of the tube 22 expands, so does the elastic sheath 30, which effectively covers the increased width presented by the slits 26 during expansion of the tip end 24.

The grasper 42 is shown further withdrawn into tube 22 in FIG. 4. In this position, the apparatus 10 is ready to be withdrawn, along with the tissue 15, from the patient's body. The elastic sheath 30 still covers and protects healthy tissue (not shown), from inadvertent contact with tissue 15 as the apparatus 10 is withdrawn from the abdominal perforation.

Another embodiment of the invention is illustrated in FIG. 5, which shows a cannula assembly 110. The assembly 110 includes a double-walled cannula 112 defining a channel 113 therethrough. The cannula 112 has a distally located tip end 101 for insertion into an abdominal cavity, and a proximally located attachment end 115 opposite the tip end 101. The attachment end 115 of the conduit 112 is attached to a conduit piece 120 by a lock element 114 configured to engage a matching lock element 122 defined by the conduit piece 120. Luer locks, friction coupling, tab engagement, snap fit attachment, threaded attachment, welded attachment (ultrasonic, RF, or thermal), adhesive attachment, or other conventional attachment methods known to those skilled in the art may be used to attach the cannula 112 to the conduit piece 120. Both removable or permanent attachment mechanisms are contemplated. Optionally, the cannula 112 can be integrally formed with the conduit piece 120.

The illustrated cannula 112 longitudinally extends for at least some portion of its length. Typically, the cannula 112 is substantially straight for it whole length, although curved, partially curved, or angled cannulas may be attached to the conduit piece 120. The cannula 112 has a tubular configuration, being formed to define a right cylinder, with its channel 113 having a circular cross section perpendicularly traverse to the longitudinally extending length of the cannula 112. However, as those skilled in the art will appreciate, the cross section of channel 113 can be elliptical, polygonal, or any other art recognized cross sectional shape.

As best shown in FIG. 6, the cannula 112 is double walled, having an outer wall 104 and an inner wall 106. These walls can be integrally formed as one piece, with longitudinally extending ribs 108 joining the walls 104 and 106, or can alternatively be separately joined, with a distinct outer wall being connected to a distinct inner wall by adhesively or weldingly attached ribs. Preferably, an extruded polymeric tube, integrally formed and cut to size, may be used to practice the present invention. For example, multiconduit tubing, supplied by Putman Plastics Corp., P.O. Box 779, Dayville, Conn., 06241, may be cut to form cannula 112. Of course, separate ribs are not necessary, since tubes, channels, or conduits can be defined in the cannula walls, or alternatively attached to the inside or outside of the cannula walls.

In the illustrated embodiment, an elastic sheath 109 is fitted over the outer wall 104 at the tip end 101 of the cannula 112. The elastic sheath 109 is substantially identical in material construction, form, and function to the elastic sheath 30 described with reference to FIGS. 1–4. In addition, the elastic sheath 109 is similarly attached, with the attachment of one side of sheath 109 to the outer wall 104 at the tip end 101. The sheath 109 is wrapped around the tip end 101 and adhesively (or weldingly, or other art recognized attachment method) attached to the inner wall 106. Like elastic sheath 30, the elastic sheath 109 provides a barrier that reduces the chance of contamination and infection of the patient as the cannula 112 is withdrawn from the patient's abdominal cavity.

The outer wall 104 of the cannula 112 is joined to the inner wall 106 by the longitudinally extending ribs 108. Between the ribs 108 are defined a plurality of longitudinally extending channels 102a, 102b, 102c, 102d, 102e, and 102f. These channels extend the length of the cannula 112 and are positioned in fluid communication with the conduit piece 120. A plurality of apertures 103a, 103b, 103c, 103d, 103e, and 103f are cut through the inner wall 106 to respectively bring channels 102a, 102b, 102c, 102d, 102e, and 102f into fluid connection with the channel 113 of the cannula 112.

Expansion of the tip end 101 of the cannula 112 is allowed by provision of a plurality of longitudinally extending slits 105a, 105b, 105c, 105d, 105e, and 105f that cut completely through the ribs 108 at the tip end 101. As shown in FIG. 7, the slits 105a-f allow expansion of the tip end 101 to accept and hold tissue 107 drawn into the cannula 112 by graspers 111.

The graspers 111 are inserted into the cannula 112 after initial insertion through a sealing assembly 150 and the intermedially located conduit piece 120. The conduit piece 120 is formed to define a first passageway 130 having first passageway walls 131, a second passageway 132 having second passageway walls 133, and a third passageway 134 having third passageway walls 135. The channel 113 of the cannula 112 is directly attached in fluid connection to the first passageway 130. The first, second and third passageways 130, 132, and 134 are dimensioned to permit passage of fluid (including air, water, saline, body fluids) and solids (including body tissue and medical instruments), including fluid drawn in through channel 113 and channels 102a-f of the cannula 112. The passageways 130, 132, and 134 are in common fluid communication, intersecting with each other at a branch 136.

Although metals such as stainless steel can be used to form the conduit piece 120, more commonly the conduit piece 120 is mold-formed as a single integral piece. Rigid thermoset plastics such as polycarbonate or polyethylene are preferred molding plastics. The low cost of molded plastics allows the conduit piece to be disposable, eliminating costly maintenance and sterilization procedures associated with manufacture of non-disposable conduits pieces. Optionally, construction of the conduit piece 120 from optically transparent plastics allows an operator to visually determine if one of the passageways 130, 132, or 134 is completely or partially blocked by solid tissue or other material.

The third passageway 134 of the conduit piece 120 is attached in fluid communication with a valving mechanism 140. The valve mechanism 140 includes a valve body 142 supporting a valve rotor 144 for ease of operation. Preferred valves are described in U.S. Pat. No. 5,019,054, to Clement et al., issued May 28, 1991, the disclosure of which is herein incorporated by reference.

Figure 8:
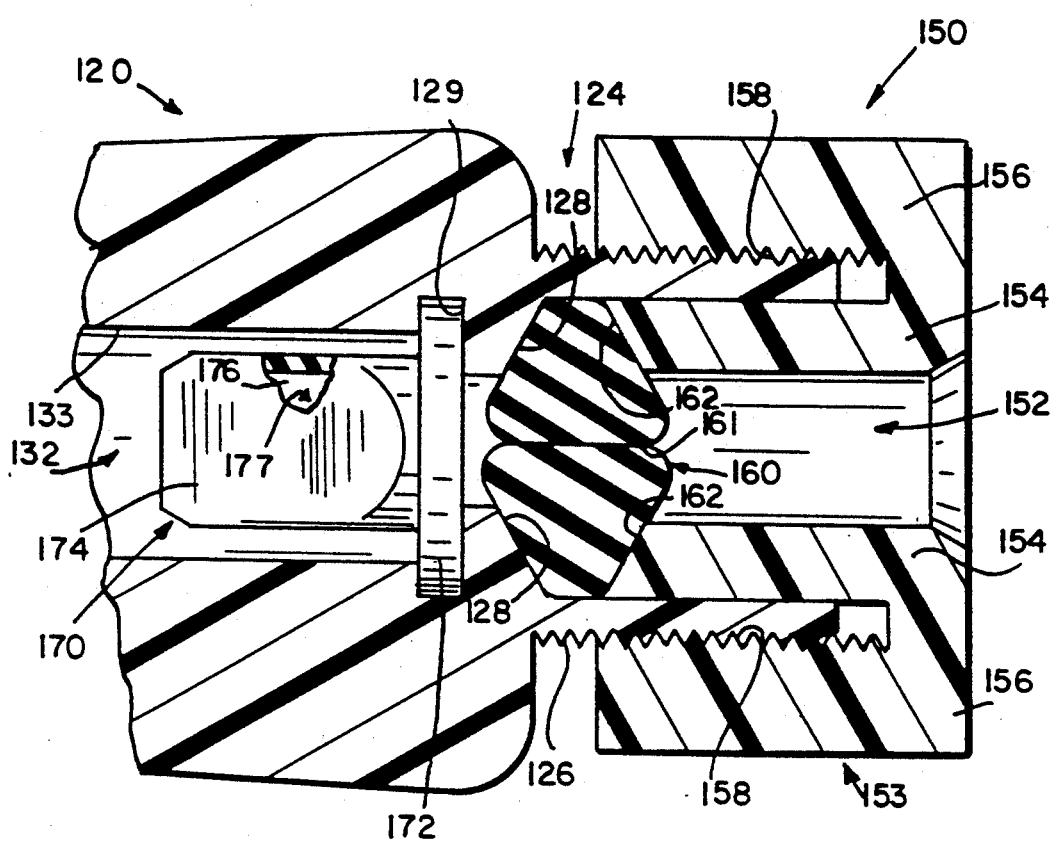
FIG. 8 is a side cross-sectional view of the sealing assembly illustrated in FIG. 5, showing complete closure of both the duckbill flap valve and the compressible annular seal.
Figure 9:
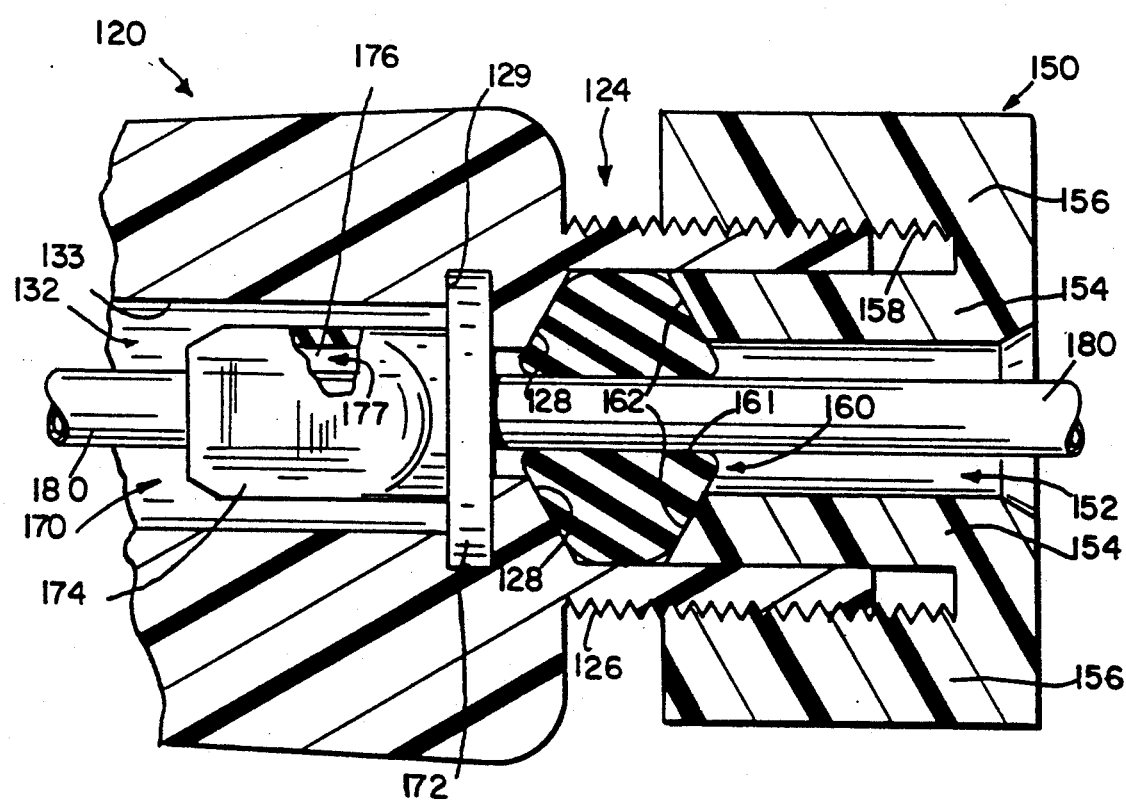
FIG. 9 is a side cross-sectional view of the sealing assembly, shown with a secondary cannula inserted through both the annular, compressible annular seal and the duckbill flap valve, the secondary cannula extending onward through the conduit piece and into the interior channel of the cannula illustrated in FIG. 5.

The sealing assembly 150 is attached in fluid connection to the second passageway 132. As best seen in FIG. 8, which is an enlarged view of the sealing assembly 150 indicated in FIG. 5, the sealing assembly 150 includes a movable compression piece 153 having connected inner and outer annular portions 154 and 156, a compressible annular seal 160, and a duckbill flap valve 170. These elements cooperate to form an airtight seal when a medical device 180 such as the secondary cannula shown in FIG. 9, or other conventional medical devices including graspers as seen in FIG. 7, tweezers, baskets, cutters, etc.) are inserted therethrough into the passageway 132 and channel 113 of cannula 112.

The compressible annular seal 160 is an annular O-ring, normally having a central aperture 161 through which medical devices can be inserted. The seal 160 is constructed of natural or synthetic polymers (e.g. rubber, neoprene, etc.) that are elastically compressible. The seal 160 is illustrated in its fully compressed state in FIG. 8, with the movable compression piece 153 inwardly moved toward the conduit piece 120 to compress the seal 60 therebetween. Optionally, the seal 160 can be coated with friction reducing compounds, including inert, biocompatible silicone oils, fluorinated polymers, or other conventional friction reducers known in the art. Such friction reducing compounds can facilitate inward or outward longitudinal movement of the medical device 180 during its positioning in, or withdrawal from, the channel 113 of the cannula 112.

The compressible annular seal 160 is positioned in a channel 152 defined by an outwardly extending neck 124. The neck 124 is an integrally formed portion of the conduit piece 120, and is formed to present external threads 126 engagable by internal threads 158 defined on the outer annular portion 156 of the movable compression piece 153. The inner annular portion 154 fits into channel 152. Clockwise rotation of the movable compression piece 153 causes a screwing movement of the movable compression piece 153 toward the conduit piece 120, compressing the seal 160 between a first annular wall 128 defined in the conduit piece 120 and a second annular wall 162 defined in the inner annular portion 154 of the movable compression piece 153. Both wall 128 and wall 162 are directed to extend at an oppositely directed (mirror image), non-perpendicular angle relative to the longitudinally extending channels 152, 113, and longitudinally extending passageway 132, to maximize sealing compression.

Those skilled in the art will appreciate that other mechanisms for compressing the compressible annular seal 160 may be employed. For example, instead of screwing mechanisms, those skilled in the art may employ ratchet mechanism, levers, or clamps to move the movable compression piece 153 closer to the conduit piece 120. In addition, perpendicularly directed walls, curved, or multiple angled walls can be used to compress the seal 160.

Situated adjacent to the compressible seal 160, and positioned in the passageway 132, is a duckbill flap valve 170. The duckbill flap valve 170 is integrally formed to have a first flap 174 biasingly directed in sealed engagement with a second flap 176. Both flaps 174 and 176 are integrally joined to a rim 172 having a central aperture 177 through which the medical device 180 can pass. The rim 172 is conformably fitted into an annular notch 129 defined in the second passageway walls 133 of the second passageway 132 to permanently hold the duckbill flap valve 170 in position. The flaps 174 and 176 are separated by a slit (not shown) that allows the flaps 174 and 176 to separate, moving apart as the medical device 180 is inserted therethrough. Like the seal 160, the flaps 174 and 176 can be coated with friction reducing compounds to ease insertion or withdrawal of the medical device 180. Additionally, as will be appreciated by those skilled in the art, other conventional multiple flap valves, including two, three, or more flap members, can be substituted for the described embodiment.

In operation, as illustrated in FIG. 3, the movable compression piece 153 is unscrewed counterclockwise until seal 160 is in a substantially uncompressed state.

The tip (not shown) of the medical device 180 is inserted through the central aperture 161 of the seal 160. The compression piece 153 is then screwed clockwise to compress the seal 160, reducing the size of central aperture 161 and consequently providing an airtight seal against the medical device 180. The movable compression piece 153 is only moved inward far enough to provide an airtight seal by compressing the seal 160, and is not moved inward far enough to lockingly engage the medical device 180. The medical device 180 is then pushed into the conduit piece 120, engaging and parting the flaps 174 and 176 of the duckbill valve. The medical device 180 can then be inserted through the second passageway 132, the first passageway 130, the channel 113 of the conduit 112, and to an operating site.

During withdrawal of the medical device 180, the tip (not shown) is brought back through the duckbill flap valve 170, allowing the flaps 174 and 176 to engage and seal against each other. Sealing engagement of the flaps 174 and 176 is encouraged by a positive pressure in the passageway 132 relative to atmospheric, but the biased construction of the flaps 174 and 176 promotes closure under neutral or even slightly negative pressures. The duckbill flap valve prevents outgassing of air or fluids (or an aerosol mixture of air and fluids) when the medical device 180 is pulled out through the central aperture 161 of the seal 160. After use, the cannula assembly 110 can be disposed of as medical waste.

As those skilled in the art will appreciate, it is not necessary to provide an intermediately located connecting piece, such as the conduit piece 120, to interconnect the cannula 112 and the sealing assembly 150. Alternatively, it is possible to directly connect the sealing assembly 150 to a conduit appropriately provided with external threads, or other conventional attachment mechanisms.

Although the invention has been described with reference to certain preferred embodiments, variations and modifications exist within the scope and spirit of the invention as described and defined in the following claims.

I claim:

1. A tissue retrieval apparatus for removal of tissue from a patient's body, the apparatus comprising
 a longitudinally extending tube having a distal tip end insertible into a patient, the distal tip end of the tube being formed to allow expansion of the distal tip end of the tube in response to withdrawal of tissue into the distal tip end of the tube,
 means for withdrawing tissue extending into the distal tip end of the tube through a conduit connected adjacent a proximal end of the tube,
 resilient sealing means in said conduit for contacting and sealing the means for withdrawing tissue in the conduit,
 an elastic sheath attached to cover the tip end of the tube to prevent contamination by withdrawn tissue, the elastic sheath being formed to expand in response to expansion of the tip end of the tube upon withdrawal of tissue into the tip end.

2. The apparatus of claim 1, wherein the longitudinally extending tube is formed to have a diameter greater than about 5 mm, and a plurality of longitudinally directed slits are defined about the distal tip end of the tube to promote expansion of the distal tip end of the tube.

3. The apparatus of claim 1, wherein the longitudinally extending tube is formed to have a diameter greater than about 5 mm, and a plurality of longitudinally directed slits are symmetrically defined in the distal tip end of the tube.

4. The apparatus of claim 1, wherein the withdrawing means further comprises a grasper reciprocally movable through the longitudinally extending tube, the grasper being formed to define a pair of movable, opposing jaws, and means for moving the jaws together to grasp tissue.

5. The apparatus of claim 4, wherein the opposing jaws are defined to have serration to aid in holding grasped tissue.

6. The apparatus of claim 1, wherein the elastic sheath is attached with an elastic adhesive to the distal tip end of the tube.

7. A tissue retrieval apparatus for removal of tissue from a patient's body, the apparatus comprising
 a longitudinally extending tube having a diameter greater than about 5 mm, a distal tip end of the longitudinally extending tube being insertible into a patient, the distal tip end of the tube being formed to define a plurality of longitudinally directed slits to allow radial expansion of the distal tip end of the tube in response to withdrawal of tissue into the distal tip end of the tube,
 a proximal end of the tube connected to a conduit,
 a resilient seal means located within the conduit,
 means for grasping tissue, the grasping means being positionable through the resilient seal means and extending into the distal tip end of the tube whereby the resilient seal means provides a seal between a portion of the grasping means and the conduit,
 means for extending the grasping means from its position in the distal tip end of the tube to grasp tissue,
 means for withdrawing the grasping means and any grasped tissue into the distal tip end of the tube, and
 an elastic sheath attached to cover the distal tip end of the tube, the elastic sheath being formed to expand in response to expansion of the distal tip end of the tube upon withdrawal of tissue into the distal tip end of the tube.

8. The apparatus of claim 7, wherein the plurality of longitudinally directed slits are symmetrically defined about the distal tip end of the tube to promote substantially even radial expansion of the distal tip end of the tube in response to retraction of the grasper into the distal tip end of the tube.

9. The apparatus of claim 8, wherein four longitudinally directed slits are defined in the distal tip end of the tube.

10. The apparatus of claim 7, wherein the withdrawing means further comprises a grasper reciprocally movable through the longitudinally extending tube, the grasper being formed to define a pair of movable, opposing jaws, and means for moving the jaws together to grasp tissue.

11. The apparatus of claim 10, wherein the opposing jaws are defined to have serrations to aid in holding grasped tissue.

12. The apparatus of claim 7, wherein the elastic sheath is attached with an elastic adhesive to the distal tip end of the tube.

13. A laparoscopy device for use in surgery processes in which an organ is severed from the body, the device comprising a tubular element for penetrating into the body, said tubular element having a proximal end portion outside the body and a distal end portion inside the body adjacent the organ to be removed, said tubular element having a central axial passageway through which various surgical instruments are inserted from outside the body to the organ to be removed, resilient sealing means in said passageway to provide a seal between the passageway and the said various surgical instruments inserted therein, said distal end portion being formed with a plurality of peripherally spaced-apart, longitudinally-extending slits to define finger portions which resiliently expand radially outwardly, a grasper inserted in the passageway as one of the various surgical instruments to pass into the tubular element for grasping the severed organ and pulling it into the distal end portion of the tubular element to be held by said finger portions, and a flexible, elastic sheath covering said distal end portion, said sheath having an open end mating with the open end of the distal end portion to prevent contamination by withdrawn tissue, so that when the severed organ is grasped and pulled into the distal end portion, said sheath encloses the distal end portion, grasper, and severed organ for removal from the body.

14. A tissue retrieval apparatus for removal of tissue from a patient's body, the apparatus comprising
a longitudinally extending cannula formed to define a channel therethrough, the cannula having an outer wall and an inner wall, and a plurality of ribs longitudinally extending to connect the outer wall and the inner wall to define channels between adjoining ribs, the cannula having a tip end insertible into a patient, the tip end of the cannula being formed to define a plurality of longitudinally directed slits to allow expansion of the tip end of the cannula in response to withdrawal of tissue into the tip end of the cannula,
means for withdrawing tissue into the tip end of the cannula, and
an elastic sheath attached to cover the tip end of the cannula to prevent contamination by withdrawn tissue, the elastic sheath being formed to expand in response to expansion of the tip end of the cannula upon withdrawal of tissue into the tip end.

15. The apparatus of claim 14, wherein the longitudinally directed slits are symmetrically defined about the tip end of the cannula to promote radial expansion of the tip end of the cannula.

16. The apparatus of claim 14, further comprising a plurality of apertures defined through the inner wall of the cannula, the apertures being defined in the tip end of the cannula and in fluid communication with the channels defined between ribs of the cannula.

17. The apparatus of claim 14, wherein the withdrawing means further comprises a conduit piece formed to define at least one passageway, the conduit piece being connected in fluid communication with the channels of the cannula.

18. The apparatus of claim 17, further comprising means for sealing the conduit piece, valve means for controlling fluid flow in the at least one passageway of the conduit piece, and wherein the conduit piece is formed to define first, second, and third passageways, the first passageway being connected to the channels of the cannula, the second passageway being connected to the sealing means, and the third passageway being connected to the valve means.

19. The apparatus of claim 18, wherein the sealing means further comprises a compressible annular seal positioned to seal the second passageway means for compressing the compressible annular seal to provide an airtight seal across the second passageway, and a duckbill flap valve positioned in the second passageway, the duckbill flap valve having a first and a second flaps biased to sealingly engage each other, the first and second flaps being configured to move apart to permit passage therethrough of a medical device inserted through the conduit piece.

20. The sealing assembly of claim 19, wherein the compressing means comprises a first annular wall defined by the conduit piece, and a movable compression piece formed to define a second annular wall, the movable compression piece being movable with respect to the conduit piece to compress the compressible annular seal between the second annular wall and the first annular wall.

21. The sealing assembly of claim 20, wherein the conduit piece is formed to define external threads, and the movable compression piece is formed to define internal threads capable of threadingly engaging the external threads of the conduit piece.

22. A tissue retrieval apparatus for removal of tissue from a patient's body, the apparatus comprising
a longitudinally extending cannula having a tip end insertible into a patient, the tip end of the cannula being formed to expand in response to withdrawal of tissue into the tip end of the cannula,
means for withdrawing tissue into the tip end of the cannula,
an elastic sheath attached to cover the tip end of the cannula to prevent contamination by withdrawn tissue, the elastic sheath being formed to expand in response to expansion of the tip end of the cannula upon withdrawal of tissue into the tip end,
wherein the withdrawing means further comprises a conduit piece formed to define at least one passageway, the conduit piece being connected in fluid communication with the cannula, and
resilient sealing means for sealing the conduit piece.

23. The apparatus of claim 22, wherein the conduit piece is formed to define first and second passageways, the first passageway being connected to the cannula and the second passageway being connected to the sealing means.

24. The apparatus of claim 23, wherein the sealing means further comprises a compressible annular seal positioned to seal the second passageway, means for compressing the compressible annular seal to provide an airtight seal across second passsageway, and a flap valve positioned in the second passageway, the flap valve comprising first and a second flaps biased to sealingly engage each other, the first and second flaps being configured to move apart to permit passage therethrough of a medical device inserted through the conduit piece.

25. The sealing assembly of claim 24, wherein the compressing means comprises a first annular wall defined by the conduit piece, and a movable compression piece formed to define a second annular wall, the movable compression piece being movable with respect to the conduit piece to compress the compressible annular seal between the second annular wall and the first annular wall.

* * * * *